United States Patent
Abeytunge et al.

(10) Patent No.: US 9,952,205 B2
(45) Date of Patent: Apr. 24, 2018

(54) SYSTEM, METHOD AND COMPUTER READABLE MEDIUM FOR IMAGING LARGE AREAS WITH MICROSCOPIC RESOLUTION

(71) Applicant: MEMORIAL SLOAN-KETTERING CANCER CENTER, New York, NY (US)

(72) Inventors: Sanjee Abeytunge, Brooklyn, NY (US); Yongbiao Li, Dobbs Ferry, NY (US); Bjorg Larson, Brooklyn, NY (US); Milind Rajadhyaksha, New York, NY (US); Ricardo Toledo-Crow, New York, NY (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 454 days.

(21) Appl. No.: 13/856,672

(22) Filed: Apr. 4, 2013

(65) Prior Publication Data
US 2013/0266980 A1   Oct. 10, 2013

Related U.S. Application Data

(60) Provisional application No. 61/620,215, filed on Apr. 4, 2012, provisional application No. 61/620,515, filed on Apr. 5, 2012.

(51) Int. Cl.
*G02B 21/00*  (2006.01)
*G01N 33/50*  (2006.01)
*G06T 3/40*  (2006.01)
*G02B 21/36*  (2006.01)
*G01N 21/64*  (2006.01)

(52) U.S. Cl.
CPC ....... *G01N 33/5091* (2013.01); *G02B 21/008* (2013.01); *G02B 21/367* (2013.01); *G06T 3/4038* (2013.01); *G01N 21/6458* (2013.01)

(58) Field of Classification Search
None
See application file for complete search history.

(56) References Cited

U.S. PATENT DOCUMENTS 6,101,265 A * 8/2000 Bacus ................ G01N 15/1475
                                                     345/665
6,711,283 B1   3/2004 Soenksen
6,819,415 B2  11/2004 Gerstner et al.
(Continued)

FOREIGN PATENT DOCUMENTS

RU        2148378 C1     5/2000

OTHER PUBLICATIONS

International Search Report for International Patent Application No. PCT/US2013/035244 dated Jul. 18, 2013.
(Continued)

*Primary Examiner* — G. Steven Vanni
(74) *Attorney, Agent, or Firm* — Stroock & Stroock & Lavan, LLP

(57) ABSTRACT

Exemplary systems, methods and non-transitory computer-accessible mediums are provided for generating a mosaic image of a large area of tissue with microscopic resolution by acquiring a plurality of rectangular-shaped long strips of images of the tissue and stitching the strips together along their lengths.

15 Claims, 9 Drawing Sheets

(56) References Cited

U.S. PATENT DOCUMENTS

| | | | |
|---|---|---|---|
| 7,155,049 B2* | 12/2006 | Wetzel | G01L 37/003 382/133 |
| 7,330,305 B2 | 2/2008 | Harris | |
| 7,476,831 B2 | 1/2009 | Juskaitis et al. | |
| 7,876,948 B2* | 1/2011 | Wetzel | G01L 37/003 348/79 |

OTHER PUBLICATIONS

International Written Opinion for International Patent Application No. PCT/US2013/035244 dated Jul. 18, 2013.
Rajadhyaksha M. et al. "Confocal examination of non-melanoma cancers in skin excisions to potentially . . . frozen histopathology" J. of Invest. Dermatology 117: 1137-1143, (2001).
Haque R. et al. "Surgical margins and survival after head and neck cancer surgery," BMC Ear, Nose Throat Disorders 6: 2, 2006.
Jacobs L., "Positive margins: The challenge continues for breast surgeons," Annals of Surgical Oncology 15(5): pp. 1271-1272 (2008).
Patel YG. et al. "Confocal reflectance mosaicing of basal cell carcinomas in Mohs surgical skin excisions" Journal of Biomedical Optics 12:3, (2007).
Tilli M. et al. "Real-time imaging and characterization of human breast tissue by reflectance confocal microscopy" Journal Biomedical Optics 12(5): (2007).
Kang D. et al. "Comprehensive imaging of gastroesophageal biopsy samples by spectrally encoded confocal microscopy" Gastrointest Endosc. 71(1) pp. 35-43 (2010).
Jain M. et al. "Modified full-field optical coherence tomography: A novel tool for rapid histology of tissues" J Pathol Inform. 2:28 (2011).
Gareau DS. et al. "Confocal mosaicing microscopy in Mohs skin excisions: feasibility of rapid surgical pathology" J. Biomedical Optics 13:5 (2008).
Gareau DS. et al. "Confocal mosaicing microscopy in skin excisions: a demonstration of rapid surgical pathology" J. Microscopy 233:1 pp. 149-159, (2009).
Gareau DS. "Feasibility of digitally stained multimodal confocal mosaics to simulate histopathology" Journal of Biomedical Optics 14:3 (2009).
Bini J. et al. "Confocal mosaicing microscopy of human skin ex vivo: spectral analysis for digital . . . simulate histology-like appearance" J. Biomedical Optics 16:7 (2011).
Gareau DS et al. "Sensitivity and specificity for detecting basal cell carcinomas in Mohs excision . . . mosaicing microscopy" J. Biomedical Optics. 14:3 (2009).
Karen JK et al. "Detection of basal cell carcinomas in Mohs excisions with fluorescence confocal mosaicing microscopy" British J. Dermatol. 160: 1242-1250, (2009).
Abeytunge S et al. "Rapid confocal imaging of large areas of excised tissue with strip mosaicing" Journal of Biomedical Optics 16:5 (2011).
Becker V. et al. "High-resolution miniprobe-based confocal microscopy in combination with video mosaicing(with video)" Gastrointestinal Endoscopy 66:5 1001-1007 (2007).
Scope A, et al. "In vivo reflectance confocal microscopy of shave biopsy wounds: feasibility of intra-operative mapping of cancer margins" Br J Dermatol. 163:6 (2010).
Al-Arashi MY, Salomatina E, Yaroslaysky AN. "Multimodal confocal microscopy for diagnosing nonmelanoma skin cancers," Lasers Surg Med 39:696-705, 2007.
K. E. Loewke, D. B. Camarillo, C. A. Jobst and J. K. Salisbury, "Real-Time Image Mosaicing for Medical Applications," Medicine Meets Virtual Reality 15 125(304-309 (2007).
Extended European Search Report for European Application No. 13772418.3 dated Sep. 17, 2015.
Abeytunge Sanjee et al: "Strip mosaicing confocal microscopy . . . excised tissue" Adv Biomed & Clinical Diagnostic Systems. vol. 8214. No. 1. (2012). pp. 1-16.
First Patent Examination Report for Australian Patent Application No. 2013243435 dated Feb. 20, 2015.

\* cited by examiner

SYSTEM, METHOD AND COMPUTER READABLE MEDIUM FOR IMAGING LARGE AREAS WITH MICROSCOPIC RESOLUTION

CROSS-REFERENCE TO RELATED APPLICATIONS

This application relates to and claims priority from U.S. Patent Application No. 61/620,215, filed on Apr. 4, 2012, and U.S. Patent Application No. 61/620,515, filed on Apr. 5, 2012, the entire disclosures of which are incorporated herein by reference.

To address this need, an exemplary approach (which can be called "strip mosaicing" herein)—which can be a faster approach—can be provided. An exemplary instrumentation utilized for strip mosaicing was recently described (See e.g., Reference 15). For example, exemplary strip mosaicing procedures can be performed with a combination of optical and mechanical scanning. The sample can be mechanically translated across an optical line allowing high aspect ratios, instead of the standard 1:1 aspect ratio of previous mosaicing procedure.

STATEMENT REGARDING FEDERALLY SPONSORED RESEARCH AND DEVELOPMENT

This disclosure was made with government support under Grant Nos. 08748 and P30CA08748 awarded by the National Cancer Institute, and Grant No. R01 EB012466 awarded by the National Institute of Health. The government may have certain rights in the present disclosure. This statement is included solely to comply with 37 C.P.R. § 401.14(f)(4) and should not be taken as an assertion or admission that the application discloses and/or claims only a particular invention.

FIELD OF THE DISCLOSURE

The present disclosure relates generally to imaging large areas, and more specifically to exemplary embodiments of systems, devices, methods and computer accessible mediums for imaging large areas with microscopic resolution.

BACKGROUND INFORMATION

An accurate and complete removal of a tumor, with minimal collateral damage to the surrounding tissue, can be guided by the examination of pathology. However, the pathology prepared, either during surgery or after, can be time consuming. In the setting of Mohs surgery of non-melanoma skin cancers, frozen pathology that can be prepared during the procedure can take 20-45 minutes per excision, and two or more excisions can be performed, which can make the total preparation time several hours (See e.g., Reference 1). In other settings, such as head-and-neck and breast cancer, surgery fixed pathology can be prepared following the surgery. Preparation of fixed sections can take at least 1-2 days. Such time delays can result in an inability to sample large amounts of tissue, and detection of residual tumor margins, in real time. Consequently, insufficient sampling of tissue, incomplete tumor removal and positive margins are reported to be between 20 to 70% of patients (See e.g., References 2 and 3). A large number of such patients subsequently undergo additional surgery, radiotherapy and/or chemotherapy. The optical imaging methods that can display nuclear morphology can offer real-time detection of tumors in large areas of freshly excised or biopsied tissue without the need for the processing that can be used in pathology. One well-known approach is based on confocal microscopy (See e.g., References 4 and 7) and another, more recent approach, is based on full-field optical coherence tomography (See e.g., Reference 8).

It can be possible to utilize confocal mosaicing microscopy procedures for imaging tumor margins in fresh tissue from surgery (See e.g., References 9 and 12). In one such exemplary embodiment, it can be possible to provide access to high-resolution images of large areas of tissue within a short time period (e.g., a few minutes).

For example, square confocal images can be collected and stitched together with custom software into a mosaic that displays a large field of view. The mosaicing of about 36×36 images (e.g., to display up to 12×12 mm$^2$ of excised tissue from Mohs surgery) can be provided in a short time frame, for example, in about 9 minutes (See e.g., References 4, 9, and 10). In a blind examination of 45 fluorescence mosaics by two Mohs surgeons, basal cell carcinoma margins were detected with an overall sensitivity of 96.6%, and a specificity of 89.2% (See e.g., References 13 and 14).

Indeed, obtaining the results in such time frame can certainly be faster than the hours or days generally required for preparing pathology; however, routine implementation in Mohs surgical settings can benefit from even faster times. In other surgical settings, excisions can be larger, and thus mosaicing by such exemplary procedure can take longer. Therefore, the adaptation of such technology to be used during surgery may not be as effective. For practical and routine utility, the exemplary mosaicing should meet the surgeons' need to examine tumor margins in large areas (e.g., ~cm$^2$) within fairly short times (e.g., ~one minute).

Thus, it may be beneficial to provide exemplary systems, methods and computer-accessible mediums that can facilitate a shorter imaging time, and/or solve at least some of the deficiencies described herein above.

SUMMARY OF EXEMPLARY EMBODIMENTS

Such needs can be addressed with the exemplary embodiments of the system, device, method and computer accessible medium for imaging large areas with microscopic resolution according to the present disclosure.

To address this need, an exemplary approach (which can be called "strip mosaicing" herein)—which can be a faster approach—can be provided. An exemplary instrumentation utilized for strip moasicing was recently described (See e.g., Reference 15). For example, exemplary strip mosaicing procedures can be performed with a combination of optical and mechanical scanning. The sample can be mechanically translated across an optical line allowing high aspect ratios, instead of the standard 1:1 aspect ratio of previous mosaicing procedure.

According to certain exemplary embodiments of the present disclosure, mechanical arrangements, electronics and software can be provided to image, for example, about 1 cm$^2$ human skin tissue in 90 seconds. An exemplary tissue translation stage can be provided which can increase and improve speed, accuracy and precision. The optical and mechanical scanning arrangement can be provided which can be synchronized to optimize alignment among strips, and image strips can be stitched during acquisition with custom software.

Previously, mosaicing on, for example, 12×12 mm$^2$ of excised tissue from Mohs surgery, and detection of basal cell carcinoma margins, was demonstrated in 9 minutes. A faster approach called "strip mosaicing" can be utilized, according to certain exemplary embodiments of the present disclosure. Exemplary strip mosaicing on, for example, 10×10 mm² of tissue was demonstrated in 3 minutes. Exemplary instrumentation, systems, methods and computer accessible mediums according to the present disclosure can be provided which can facilitate mosaicing of about 10×10 mm² tissue in about 90 seconds. For example, rapid mosaicing of confocal images on large areas of fresh tissue can offer a way to perform pathology at the bedside. Thus, exemplary strip mosaicing confocal microscopy procedures can serve as an adjunct to pathology for imaging tumor margins to guide surgery.

Exemplary systems, methods and non-transitory computer-accessible mediums can be provided for generating an image of at least one tissue that can be subdivided into a plurality of strips. Using such exemplary systems, methods and computer-accessible mediums, it is possible to scan, using an optical arrangement to generate first information, a first portion of the tissue(s) along a first one of the strips while the tissue(s) can be mechanically moved in a first direction; move the tissue(s), by a distance equal to or less than a width of the first portion, in a second direction approximately perpendicular to the first direction; and scan, using the optical arrangement to generate second information, a second portion of the tissue(s) along a second one of the strips while the tissue(s) can be mechanically moved in a third direction, which can be approximately opposite to the first direction. Then the image can be generated based on the first information and the second information.

According to further exemplary embodiments of the present disclosure, the moving procedure can be performed without scanning the at least one tissue. The first portion can be scanned from a proximal end of the first strip to a distal end thereof, and the second portion can be scanned from a distal end of the second strip to a proximal end thereof. The scanning of the first portion and the second portion can be performed without stopping, and the scanning of the first portion and the second portion can be performed during a continuous and uninterrupted motion of the tissue(s).

In additional exemplary embodiments of the present disclosure, the scanning of the first portion and the second portion can be synchronized with the moving of the tissue(s). In some exemplary embodiments of the present disclosure, the first strip and the second strip can be rectangularly shaped, and the rectangularly shaped first strip and second strip each can have an aspect ratio of approximately 1:25. The image can be generated using a mosaicing procedure, which can include stitching together the first information and the second information.

In a further exemplary embodiment of the present disclosure, a system can be provided for generating an image of a tissue(s). The exemplary system can include an optical scanning arrangement configured to scan a strip of the tissue(s), and a mechanical arrangement configured to move the tissue(s) when the strip of the tissue(s) can be scanned by the optical arrangement. An imaging arrangement can also be provided which can be configured to generate the image based on information received from the optical scanning arrangement.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which.

Figure 1A:
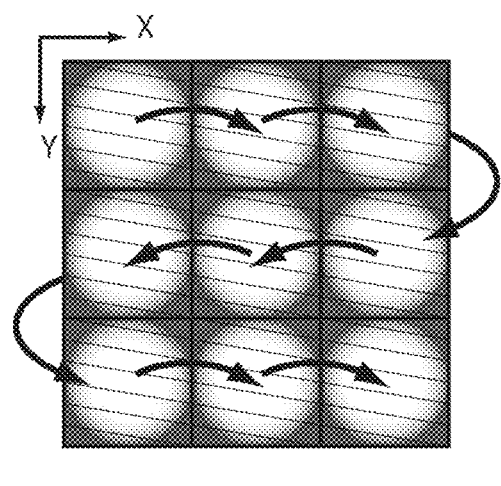
FIG. 1A is an exemplary schematic diagram illustrating exemplary mosaicing of square-shaped images in two dimensions.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures, or the appended claims.

DETAILED DESCRIPTION OF EXEMPLARY EMBODIMENTS

Figure 1B:
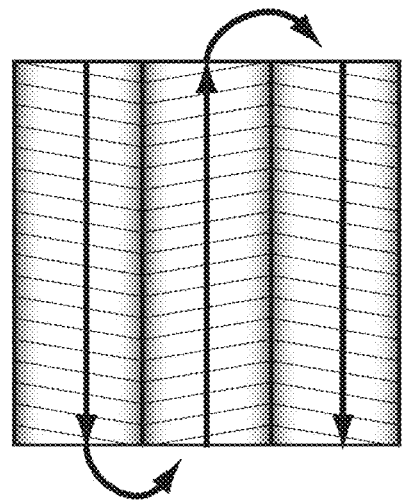
FIG. 1B is an exemplary schematic diagram illustrating exemplary mosaicing of rectangular-shaped long strips in one dimension according to an exemplary embodiment of the present disclosure.

Certain exemplary mosaicing procedures are performed by stitching square-shaped images, for example, with a standard 1:1 aspect ratio, in two dimensions, as shown in FIG. 1A. According to exemplary embodiments of the present disclosure, it can be possible to utilize a further exemplary mosaicing procedure which can acquire rectangular-shaped long strips of images, with, for example, a 1:25 aspect ratio for approximately 10 mm long strip, and stitches along the length of the strip, as shown in FIG. 1B. For example, an elimination of a dimension can reduce the acquisition time, stitching time and the artifacts due to illumination fall-off, for example, by about 50%.

Figure 2:
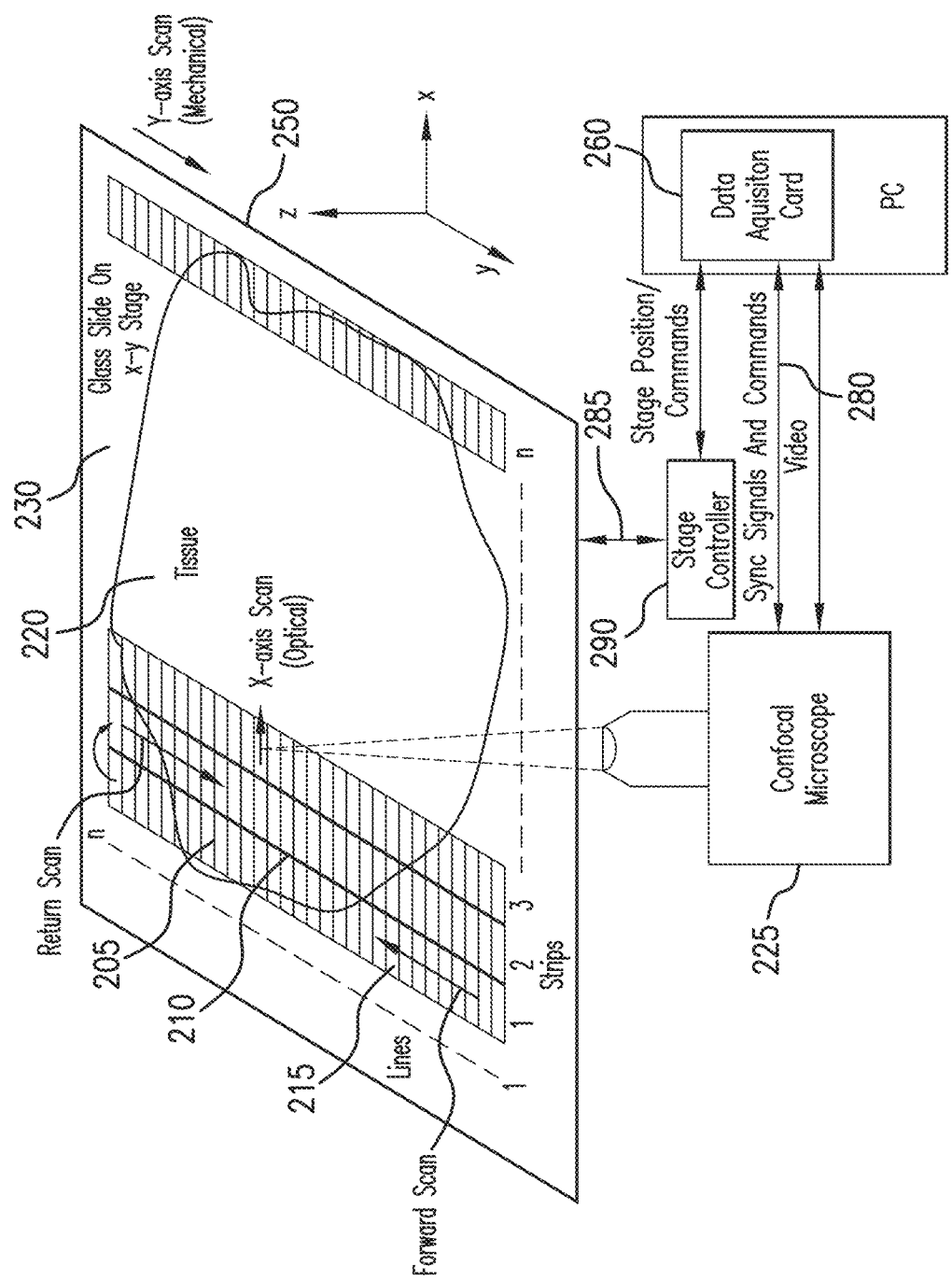
FIG. 2 is an exemplary schematic diagram of an exemplary strip-scanning mechanism and/or procedure according to an exemplary embodiment of the present disclosure.
Figure 8:
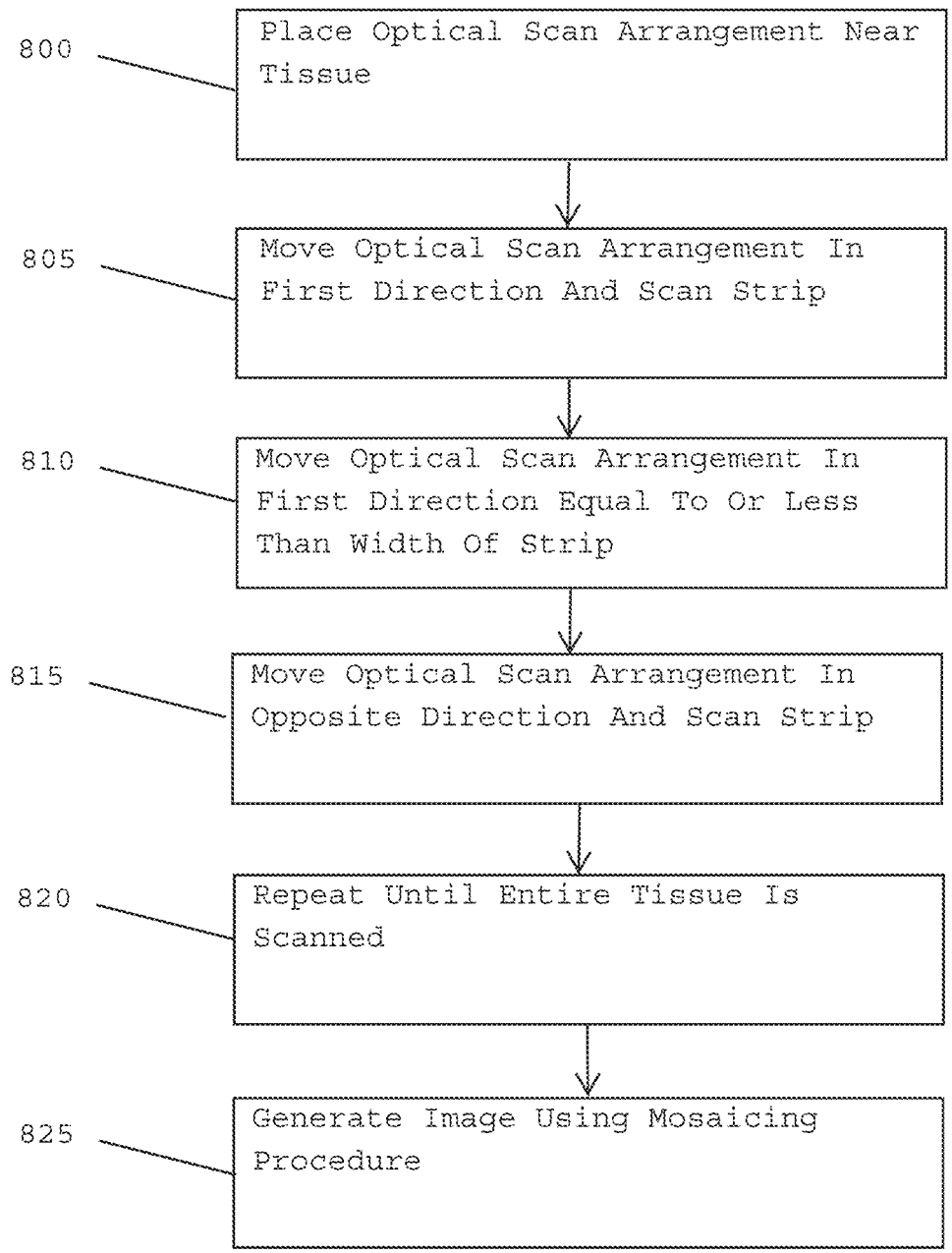
FIG. 8 is an exemplary flow diagram for imaging at least one tissue according to an exemplary embodiment of the present disclosure.

A combined optical and mechanical scan strip mosaicing procedure/apparatus, according to exemplary embodiments of the present disclosure, can be seen in the exemplary illustration of FIG. 2, which can show a fast optical scan procedure that can image a line 205 (e.g., in x-direction) along the width of a strip (e.g., x-axis) (see, e.g., FIG. 8—Procedure 800). This exemplary line can be scanned along the length of the strip 210 (e.g., y-axis) by translating the stage 250 in the direction orthogonal to the optical line (see, e.g., FIG. 8—Procedure 805). When the acquisition of a strip image 215 is completed (e.g., "forward scan" in y-direction), the stage 250 can step through a distance equal to or less than the width of the strip in the x-direction (see, e.g., FIG. 8—Procedure 810). Then, the stage 250 can translate along the length, e.g., in the direction opposite (e.g., "return scan") to the previous scan, and another strip image can be acquired (see, e.g., FIG. 8—Procedure 815). This process of acquiring strip images, cyclically in opposite y-directions (e.g., forward scan followed by return scan), can be repeated until the entire tissue 220 can be imaged (see, e.g., FIG. 8—Procedure 820).

Exemplary Instrumentation

Exemplary Confocal Microscope

According to an exemplary embodiment of the present disclosure, it can be possible to provide exemplary system, method, and computer-accessible medium which can utilize a modified breadboard version of a commercially-available confocal microscope 225 (e.g., Vivascope 2000, Lucid Inc., Rochester, N.Y.). The exemplary microscope can be modified to image in two modes, reflectance and fluorescence, and can have two or more detector channels. Exemplary control commands can be transmitted to the microscope's control system, for example, via a RS-232 port, or other suitable communication mechanism. The exemplary microscope can be provided in an inverted configuration that can be designed to image excised or biopsied tissue ex vivo. The illumination can be performed with, for example, a 488 nm laser with power of ~5 mW on the tissue. The exemplary 24-sided polygonal mirror can be used to scan the laser in the x-direction sweeping a line at ~8.9 kHz through a 30×, 0.9 numerical aperture ("NA") water immersion objective lens (e.g., Stableview, Lucid Inc.). The length of the line can be 485 µm. The lateral resolution, per Rayleigh criterion, can be about 0.33 µm (Airy radius) and the optical sectioning can be about 1.61 µm. The exemplary objective lens can be custom-designed to image through a 1-mm-thick glass slide. In normal operation, this line can be scanned in the orthogonal direction (e.g., y-direction) by a galvanometrically-driven mirror to produce a square-shaped image. To acquire a long rectangular-shaped strip image stop the galvanometric scan can be stopped and "lock" the position of the polygon-scanned line on the optical axis.

Exemplary Tissue Preparation and Mounting

Exemplary tissues used from Mohs surgery and staining methods have been extensively described (See e.g., References 9 and 12). The staining of nuclear morphology can be accomplished by soaking the tissue in, for example, 0.6 mM acridine orange for about 30 seconds followed by rinsing the excess with isotonic phosphate buffered saline solution.

Fresh tissue 220 from surgery can present irregular shapes and topography, and variable sizes. Imaging of large areas of such tissue to create mosaics can benefit from accurate and repeatable mounting. A tissue fixture can be engineered for mounting Mohs surgical excisions and to control the position, flatness and orientation of the surface to be imaged. The fixture can be mounted on to a translation stage 250, and the stage can be fitted to the microscope breadboard with a custom-made holder.

The tissue 220 can be placed on the glass window 230 of the fixture and imaged through it. An acquisition of a large number of images over a large area at a constant depth can use imaging and scanning planes parallel to each other. This parallelism can be obtained by adjusting the tip-tilt adjustments of the tissue fixture in an iterative manner, and observing images of the glass window at four corners. When the images at the four corners appear uniform and identical to each other, the image plane can be parallel to the x-y scan plane.

The exemplary mechanical specifications of the translation stage such as straightness, flatness, repeatability and accuracy can be exemplary factors for long strip scans. It can be possible to use a high-quality dual-axis stage (e.g., BioPrecision2, Ludl Electronics, Hawthorne, N.Y.) to mechanically scan (e.g., translate) the tissue with respect to the objective lens. The straightness and flatness of this stage can be about 1 µm/25 mm. Therefore, for a scan (e.g., translation) of 10 mm travel, for example, the maximum deviation in straightness can be 0.8 µm between any two strips. This can be well within the overlap between any two strips. The maximum deviation in flatness can also be within the optical sectioning of about 1.61 µm.

The exemplary translation stage 250 can be equipped with a linear encoder. The exemplary encoder can be read via its controller (e.g., MAC5000, Ludl). The encoder outputs can be sent to a fast data acquisition ("DAQ") card 260 (e.g., via syncronization signals 280) for synchronization in real time. The commands 285 to initiate and control the movement of the stage 250 can be transmitted to a controller 290 through a USB bus, or other suitable communication mechanism.

Exemplary Synchronization of Strips in the Y-Direction

The mechanical scan by the translation stage (e.g., slow scan in Y-direction) can be driven by a stepper-motor without a position encoder. It can be possible to accomplish the synchronization of the optical scan by the polygon (e.g., fast scan in X-direction) and the mechanical scan by the translation stage (e.g. slow scan in Y-direction) by counting the step-pulses from an exemplary stepper-motor. A mismatch of up to 75 lines, between any two strips, can be observed, which can result from missing steps, and the lack of position accuracy. This mismatch can be corrected during stitching of the strips, although at the expense of a likely high demand for computer processing power and increased time for creating mosaics. Therefore, position synchronization in Y-direction can be important to reduce the work of the stitching procedure, and to reduce the time used for mosaicing. The exemplary synchronization mechanism, according to an exemplary embodiment of the present disclosure, can facilitate that the maximum expected mismatch between any two strips to be, for example, one line in the Y-direction, and zero pixels between any two lines within a strip.

Figure 3:
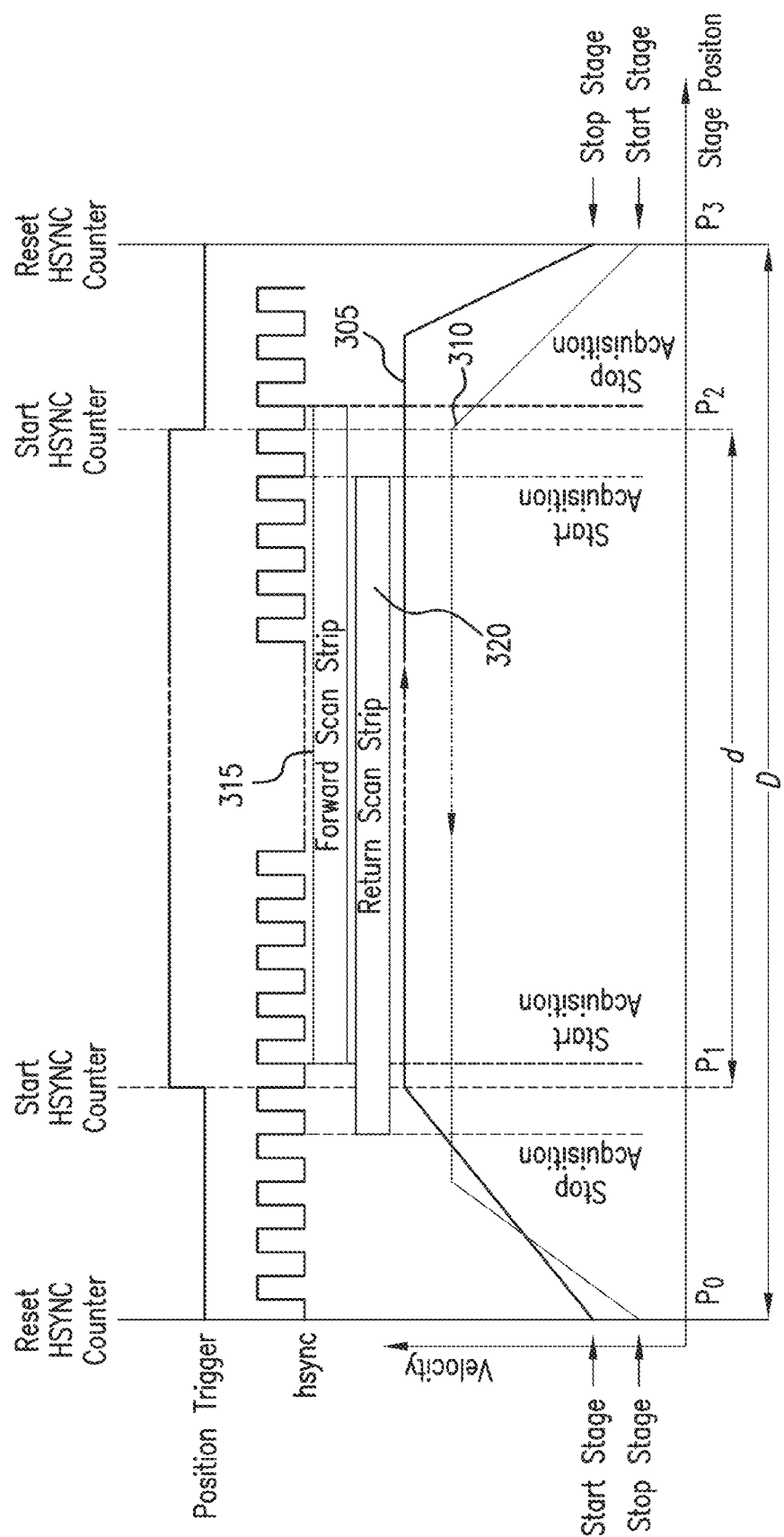
FIG. 3 is an exemplary signal diagram illustrating an exemplary synchronization for strips according to an exemplary embodiment of the present disclosure.

FIG. 3 shows an exemplary signal diagram provided by an exemplary synchronizing procedure for the strips, in accordance with an exemplary embodiment of the present disclosure. For example, a Y-translation stage cycle can include two or more mechanical scans that produce two or more image strips, for example, the "forward scan" $P_0$ to $P_3$ (e.g., velocity profile 305) and the "return scan" $P_3$ to $P_0$ (velocity profile 310). An image strip 315 can be acquired during the forward scan. Then, the stage can step or translate through, for example, about 400 µm, which can be less than the line length 485 µm, or the width of a strip, in the X-direction, and another image strip 320 can be acquired on the return scan.

Since the acceleration and deceleration profiles of the exemplary translation stage for forward and return scans can be different (e.g., as depicted in FIG. 3), the image can be acquired within the constant velocity portion of both scans. This can avoid a distortion of the mosaic due to compression or elongation of pixels. Therefore, it can be possible to select a scan distance (D) for the Y-translation stage such that the region of constant velocity section (d) can be larger than the size of the tissue excision, as shown in FIG. 3. According to an exemplary embodiment, it can be possible to first determine the positions $P_0$, $P_1$, $P_2$, and $P_3$ by observing the velocity profiles of the Y-translation stage through one cycle. When the coordinates can be known, it can be possible to scan the sample and acquire images.

Figure 4:
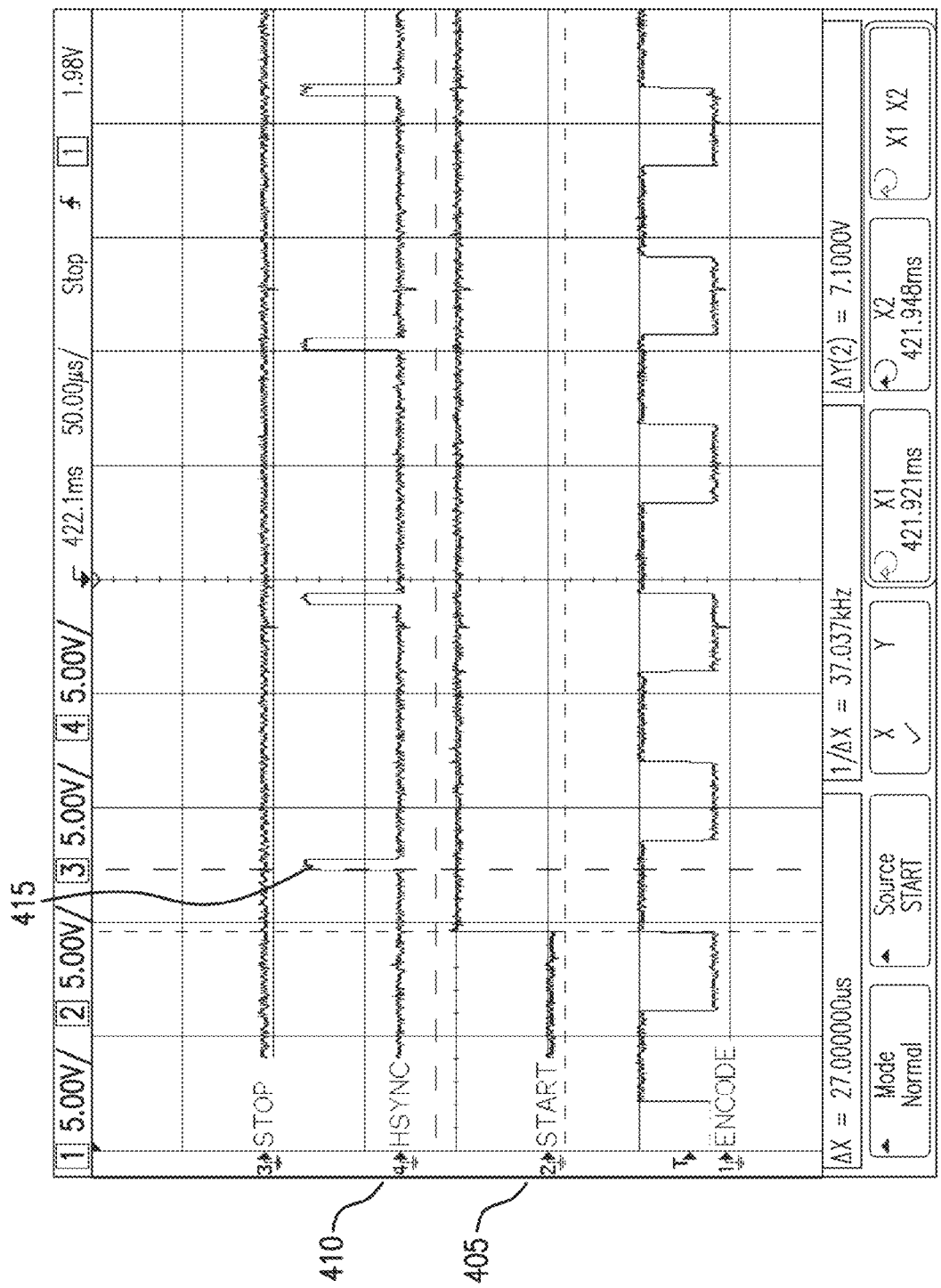
FIG. 4 is an exemplary signal diagram provided by an oscilloscope trace of the front end of a scan of a strip according to an exemplary embodiment of the present disclosure.
Figure 5:
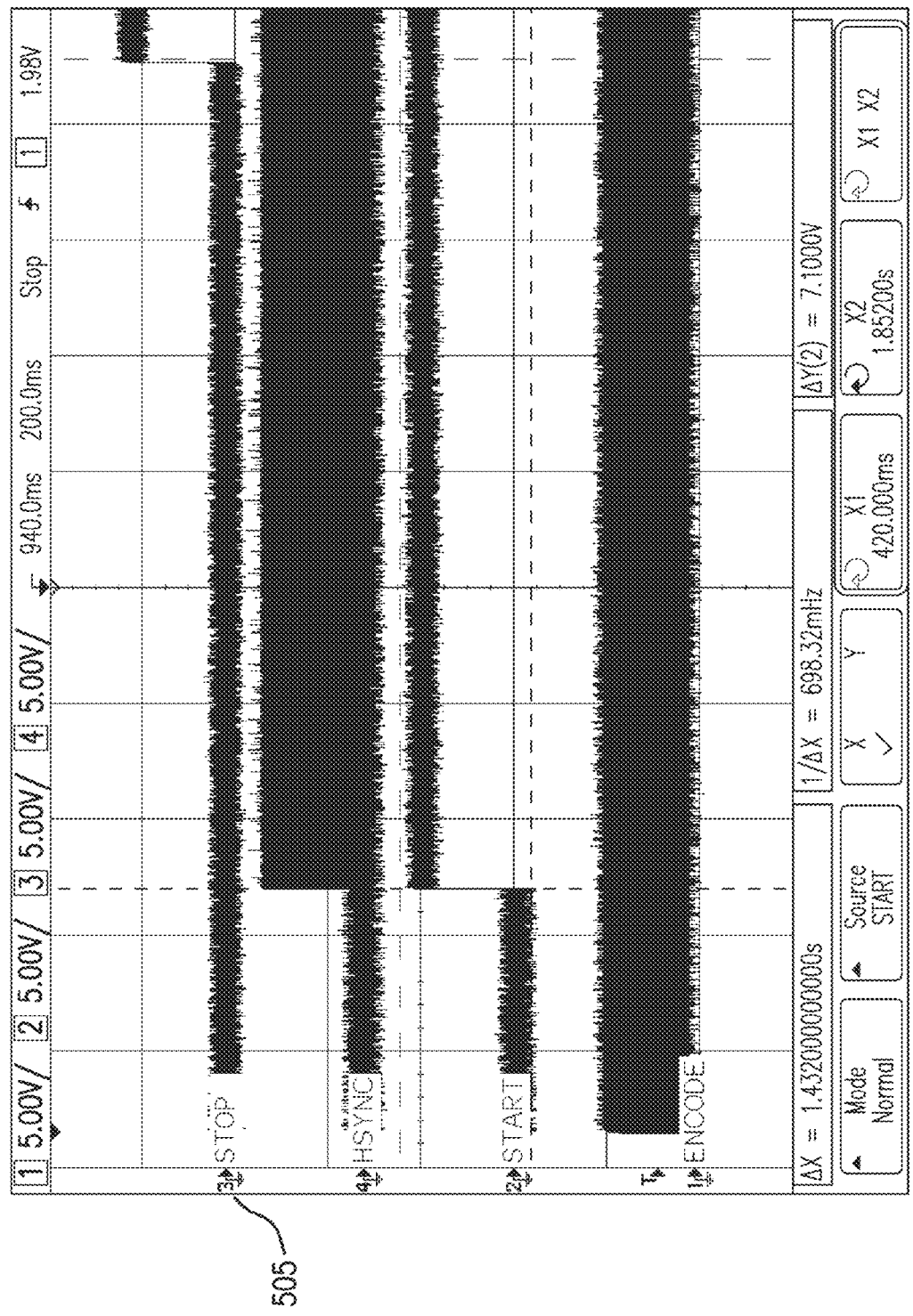
FIG. 5 is an exemplary signal diagram provided by an oscilloscope trace of the back end of a scan of a strip according to an exemplary embodiment of the present disclosure.

A graph of exemplary oscilloscope traces of the timing procedure, for example, the front portion of the scan, is shown in an exemplary signal diagram of FIG. 4. For example, after the forward scan can be initiated, the data acquisition card can monitor the stage positions $P_0$, $P_1$, $P_2$, and $P_3$ in real time via the encoder and stage controller. When the stage reaches $P_1$, the "start" signal 405 can be asserted to arm the counter which monitors horizontal synchronization ("HSYNC") pulses 410. When the HSYNC-counter receives its first HSYNC pulse 415, it can trigger another counter to generate a pixel clock ("PCLK"). The PCLK can sample the analog input video signal creating the first line of the image in the strip. A number of PCLK pulses to be generated by the counter can be predefined. When the counter reaches the predefined value, it can reset and wait for the next HSYNC pulse to repeat the process. This exemplary process can continue until the Y-translation stage reaches position $P_2$. At $P_2$ the "stop" signal (see signal 505 of FIG. 5) can be asserted, and the HSYNC counter can be stopped. However, the image acquisition can continue until the PCLK counter reaches its predefined value, thus completing the last line in the strip image. At the end of Y-translation stage travel at $P_3$, the HSYNC counter can be reset. The X-translation stage can then step or translate in the X-direction to a predetermined value, which can set the width of the strip. The return scan can be initiated from $P_3$ to $P_0$, and can follow, for example, a similar mechanism to the forward scan. This exemplary cyclical process, forward scan and return scan, can be repeated until the entire tissue can be imaged.

Exemplary Acquisition of Mosaics

The exemplary acquisition time can be restricted by the speed of the optical (e.g., polygon) scanning rate of, for example, ~8.9 kHz. Since the exemplary lateral resolution can be about 0.33 μm, adequate sampling can utilize the speed of the stage as being less than about 2.9 mm/s (e.g., 0.33 μm×8.9 kHz). However, the stage can be scanned at approximately 8.5 mm/s to reduce the mosaicing time and thus under-sample by a factor of approximately 6. This can result in a pixel size of approximately 1 μm in both X and Y directions. An exemplary resolution of about 1 μm can be adequate for the interpretation of images by surgeons and pathologists [15]. When the Y-scan is completed, the X-stage can move, for example, about 400 μm laterally, leaving approximately a 17% overlap between any two strips. It can be possible to repeat this exemplary procedure until, for example, the sample can be fully scanned.

The fluorescence images can be captured with, for example, a fast DAQ card (e.g., PCI-6115 and Labview, National Instruments, Austin Tex.). The captured image strips can be stitched according to the exemplary methods and procedures according to exemplary embodiments of the present disclosure.

Exemplary Stitching

An exemplary stitching procedure according to an exemplary embodiment of the present disclosure (e.g., which can be written in or utilize Matlab, R2011a, Mathworks, Inc.) can be provided to automatically register image strips in the order in which they can be collected. Strips can be registered pair-wise, and then stitched together into one mosaic. A phase correlation method can be selected for speed and ease of implementation, as can be determined by Fast Fourier Transform ("FFT"). An exemplary correlation between the images can be maximized when features in the subject images can be properly overlapped. However, the phase correlation can be biased towards solutions near zero offset between the two images, and so the bias can be removed in the x-direction by dividing the cross correlation by a triangle function. The removal of the bias can emphasize the noise near the edges of the cross correlation. Thus, for example, about 30 pixels near the edges of the cross-correlation can be excluded from the search region, as solutions in that region of maximum offset may not be expected. Along the y-direction, as solutions near zero offset can be expected, the removal of the bias can be unnecessary, and can likely serve to emphasize the noise. Generally, a window function can be applied to an image before performing a phase correlation algorithm to reduce high-frequency edge effects. However, according to an exemplary embodiment of the present disclosure, the illumination falloff due to optical vignetting across the strips can serve this purpose, and thus, the illumination falloff can be corrected after an exemplary registration procedure can be applied.

According to an exemplary embodiment of the present disclosure, the falloff can be corrected by averaging each strip along its length, normalizing that average to one, and then dividing each line in that strip by the normalized average falloff along the strip. Because the laser illumination can be constant throughout the acquisition of the mosaic, the signal level of each strip can be properly related to its neighbors, and therefore dividing by the normalized average falloff can preserve the signal level of each strip with respect to its neighbors. The entire mosaic can be resealed to attain a full range of brightness levels.

In the exemplary overlap region between strips, the strips can be blended by a weighted average of the overlapping pixels determined by the pixel distance to the edge of the strip. Pixels close to the edge of the strip can be weighted less than pixels far from the edge of the strip. An exemplary result can be, for example, a seamless mosaic.

To reduce the total time for the acquisition and stitching of the mosaics, an exemplary embodiment of the stitching procedure can be run simultaneously with the exemplary acquisition. For example, as each strip is acquired, it can be saved into a directory, which can be polled, for example, every few seconds (e.g., three) by the exemplary stitching procedure. When two or more strips have been collected, they can be registered and blended together into the mosaic, which can be displayed on the screen so that the operator can view the progress of the exemplary acquisition. As each new strip is collected, it can be registered to the previous strip, and blended into the mosaic. Therefore, the exemplary registration and blending of the mosaic strips do not add additional time to the total mosaic acquisition time.

Exemplary Results

Figure 6:
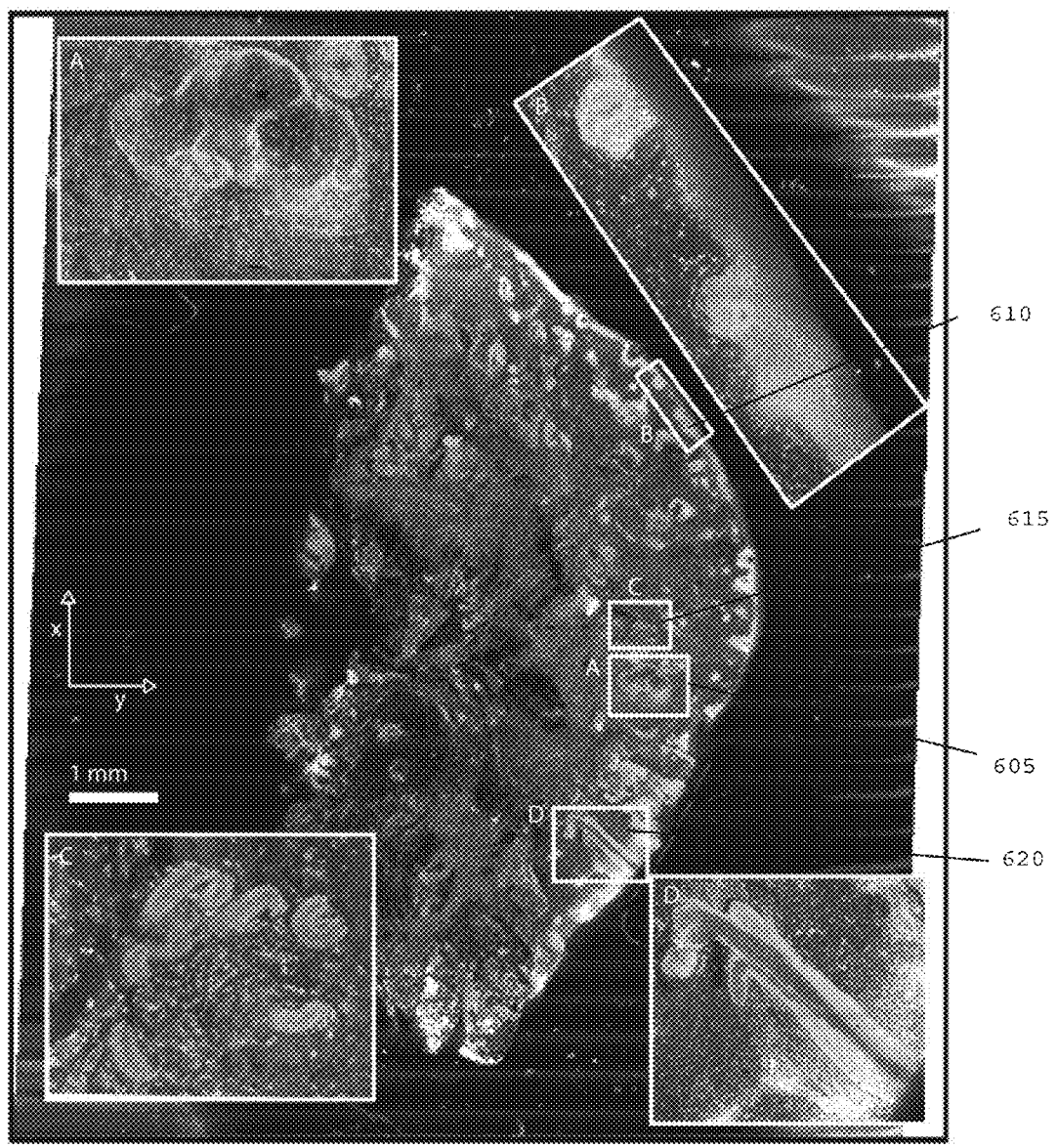
FIG. 6 is an exemplary image illustrating a mosaic having a particular exemplary number of fluorescence image strips excised tissue from an exemplary Mohs surgery according to an exemplary embodiment of the present disclosure.

FIG. 6 shows an exemplary image of a strip mosaic of a skin excision from Mohs surgery. An exemplary measured time for scanning a 30-strip 12×10 mm² mosaic can be about 130 seconds. Stitching and blending of the 30 strips after completing the acquisition can take about 54 seconds.

Figure 7:
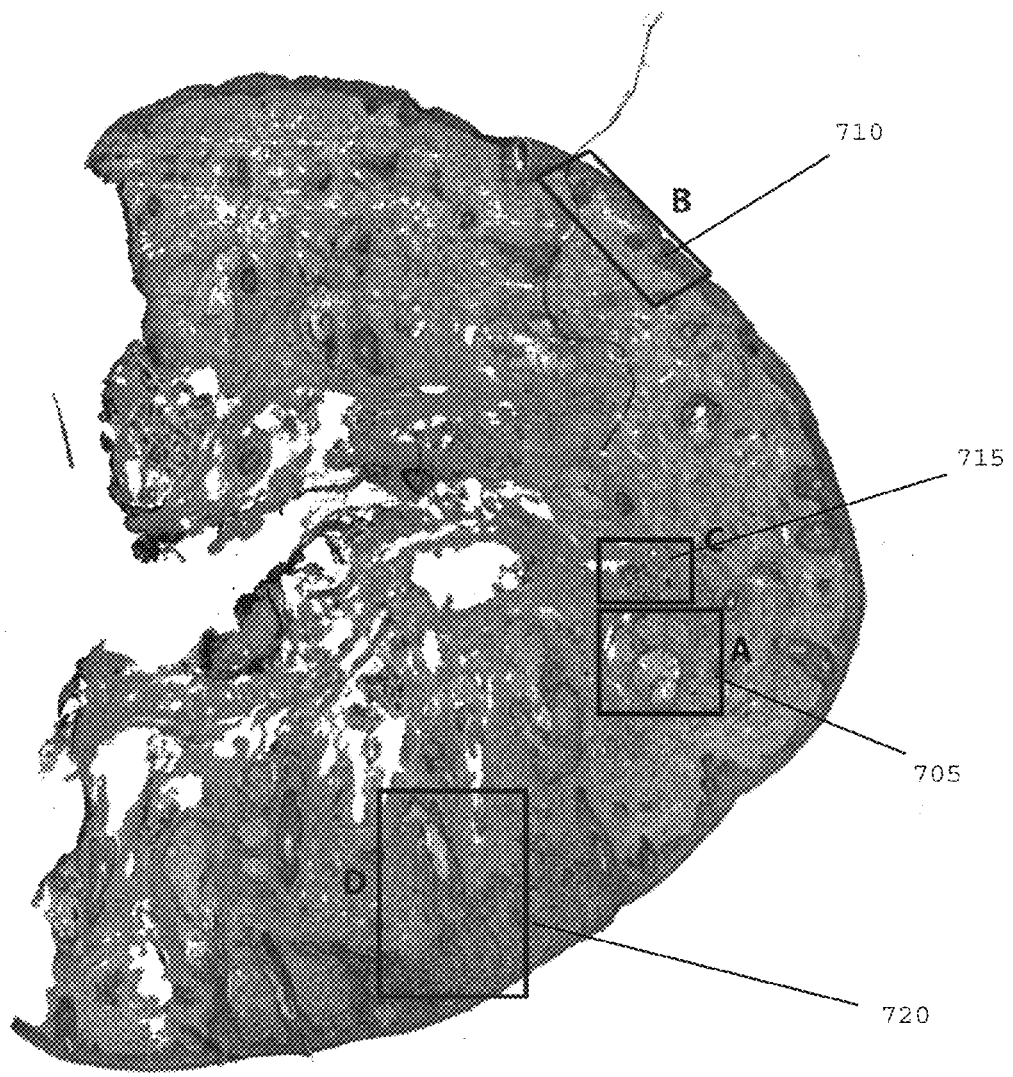
FIG. 7 is an exemplary image of a frozen Hematoxylin and eosin ("H&E")-stained pathology of excised tissue from an exemplary Mohs surgery according to an exemplary embodiment of the present disclosure.

Therefore, the total time for 12×10 mm² mosaic can be approximately 3 minutes. Features such as, for example, sebaceous glands 605, epidermis 610, eccrine ducts 615 and hair follicle 620 can be seen in FIG. 6. The mosaic dimensions can be 13,035 pixels in the X-direction and 10788 pixels in the Y-direction with a pixel depth of 8 bits. The magnified areas can be digital zooms from the original image showing detail and resolution of the mosaic. The features of FIG. 6 can be compared to the pathology of FIG. 7, which illustrates a frozen Hematoxylin and eosin ("H&E")-stained pathology of excised tissue from Mohs surgery for sebaceous glands 705, epidermis 710, eccrine ducts 715 and hair follicle 720, where the wide-field microscopy images correspond to a tissue slice adjacent to the tissue slice of FIG. 6.

Using an exemplary embodiment of the present disclosure, which can utilize exemplary stage profiles, it can be possible to scan, e.g., about 18 mm in the Y-direction (D in FIG. 3) to acquire data for, for example, about 10 mm (d in FIG. 3). The exemplary Y-scan and the exemplary lateral movement in X-direction can take approximately 3 seconds. Such time can be further reduced using an exemplary embodiment of a stage profile, for example, with reduced D with shorter acceleration ramps.

For example, at about 8.5 mm/s scan speed in Y, it can be possible to achieve approximately 18 mm scan in about 2.1 seconds, and leave another approximately 0.5 seconds for lateral movement. This can leave about 2.5 seconds total time for a strip. The additional half of a second per strip can be due to the DAQ card setup times. This time delay can also be eliminated or reduced using electronics according to certain exemplary embodiment of the present disclosure.

FIG. 6 shows the exemplary systematic Y-offset along the X-direction. This offset can be due to the optical scanning axis (X) not being perpendicular to the mechanical scanning axis (Y). Since this possible error can be a constant, it can be simply corrected using an exemplary embodiment of the stitching procedure according to the present disclosure.

Exemplary strip mosaicing confocal microscopy procedures can offer an imaging technology platform for real time detection of tumor margins directly in fresh tissue during surgery and from biopsies. Large amounts of tissue can be examined for, for example, tumor margins rapidly enough to be of practical use in surgical and clinical settings. The exemplary imaging can potentially be developed into an adjunct for pathology, to facilitate more complete and accurate removal of tumor.

Exemplary embodiments of strip mosaicing procedures implemented on tissue from Mohs surgery in skin cancer described and shown herein can be used in surgical settings. Such exemplary embodiments can be applied in and for other tissues, not only for surgical settings but also in clinics for screening of biopsies.

Beyond imaging on excised tissue, the exemplary system, method and computer-accessible medium, according to exemplary embodiments of the present disclosure, can be implemented directly on patients to delineate tumor margins, either preoperatively or intraoperatively in surgical wounds. Preliminary feasibility of such techniques has been reported for mosaicing on skin in vivo (See e.g., References 16 and 17) and also in shave-biopsied wounds in which residual tumor (e.g., basal and squamous cell carcinoma) margins can be delineated (See e.g., Reference 18). Such exemplary embodiments can utilize exemplary mosaicing procedures, both on excised tissue at the bedside and intraoperatively on the patient, which can prove useful for detection of tumor margins in a rapid, efficient and cost-effective manner.

The exemplary system, method and computer-accessible medium, according to exemplary embodiments of the present disclosure, can have a focused line that can include a cylindrical lens and objective lens (e.g., or any other arrangement to provide the exemplary focused line). For example, the line can be focused on tissue. The tissue can be translated back and forth, and light in reflectance and/or fluorescence can be collected onto and/or detected by a single, a pair or a further plurality of linear detectors. According to exemplary system, method and computer-accessible medium, such exemplary light can also be collected on or by, or detected by, a single line of pixels on a 2d detector arrangement. It can also be possible to exclude scanners altogether. The dual reflectance and fluorescence detection can facilitate an exemplary implementation of various digital staining procedures.

Figure 9:
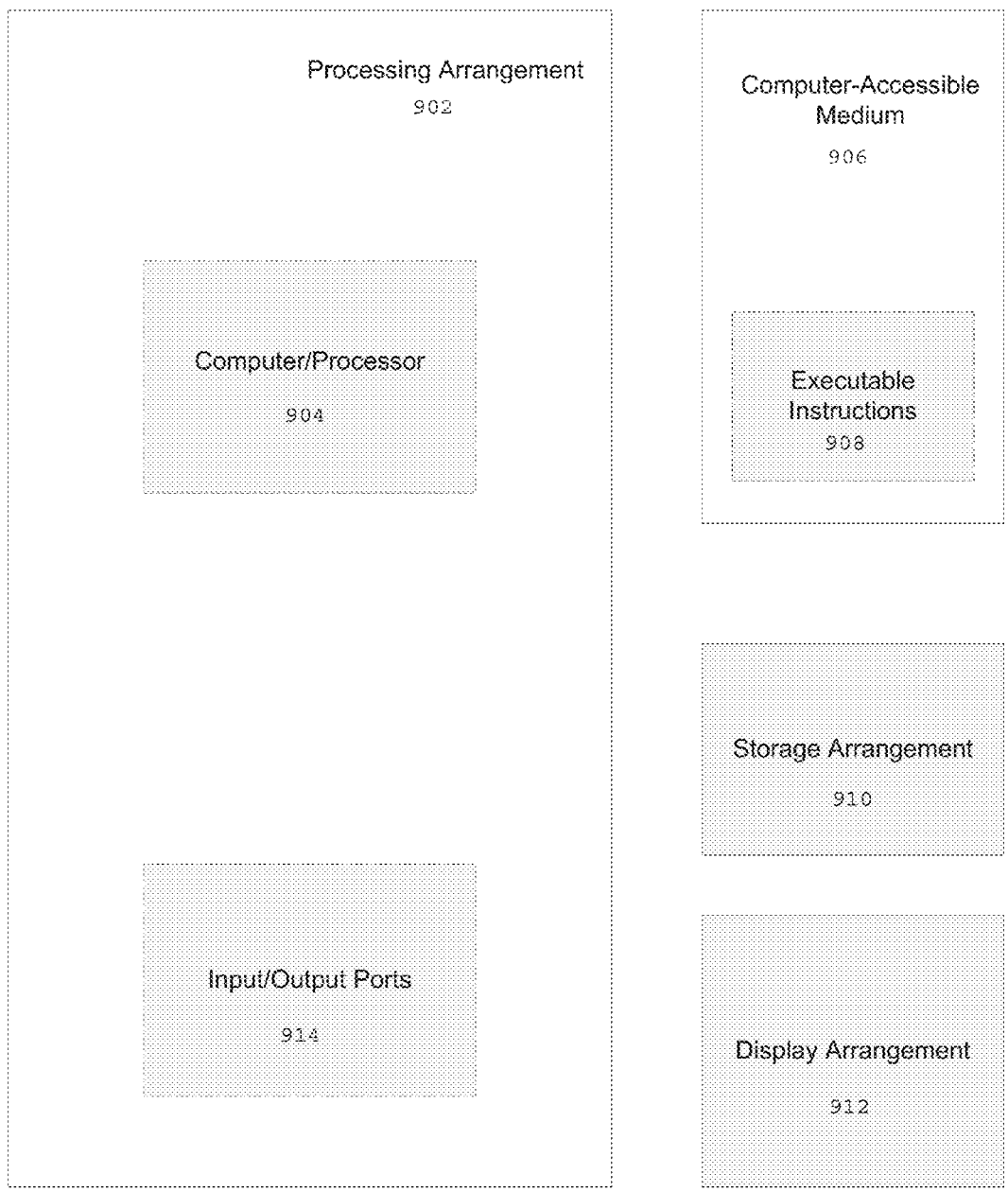
FIG. 9 is an illustration of an exemplary block diagram of an exemplary system in accordance with certain exemplary embodiments of the present disclosure.

FIG. 9 shows a block diagram of an exemplary embodiment of a system according to the present disclosure. For example, exemplary procedures in accordance with the present disclosure described herein can be performed by a processing arrangement and/or a computing arrangement 902. Such processing/computing arrangement 902 can be, for example, entirely or a part of, or include, but not limited to, a computer/processor 904 that can include, for example, one or more microprocessors, and use instructions stored on a computer-accessible medium (e.g., RAM, ROM, hard drive, or other storage device).

As shown in FIG. 9, for example, a computer-accessible medium 906 (e.g., as described herein above, a storage device such as a hard disk, floppy disk, memory stick, CD-ROM, RAM, ROM, etc., or a collection thereof) can be provided (e.g., in communication with the processing arrangement 902). The computer-accessible medium 906 can contain executable instructions 908 thereon. In addition or alternatively, a storage arrangement 910 can be provided separately from the computer-accessible medium 906, which can provide the instructions to the processing arrangement 902 so as to configure the processing arrangement to execute certain exemplary procedures, processes and methods, as described herein above, for example.

Further, the exemplary processing arrangement 902 can be provided with or include an input/output arrangement 914, which can include, for example, a wired network, a wireless network, the internet, an intranet, a data collection probe, a sensor, etc. As shown in FIG. 9, the exemplary processing arrangement 902 can be in communication with an exemplary display arrangement 912, which, according to certain exemplary embodiments of the present disclosure, can be a touch-screen configured for inputting information to the processing arrangement in addition to outputting information from the processing arrangement, for example. Further, the exemplary display 912 and/or a storage arrangement 910 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. In addition, all publications and references referred to above can be incorporated herein by reference in their entireties. It should be understood that the exemplary procedures described herein can be stored on any computer accessible medium, including a hard drive, RAM, ROM, removable disks, CD-ROM, memory sticks, etc., and executed by a processing arrangement and/or computing arrangement which can be and/or include a hardware processors, microprocessor, mini, macro, mainframe, etc., including a plurality and/or combination thereof. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it can be explicitly being incorporated herein in its entirety. All publications referenced can be incorporated herein by reference in their entireties.

EXEMPLARY REFERENCES

The following references are hereby incorporated by reference in their entirety.
1. Rajadhyaksha M, Menaker G, Dwyer P J, Flotte T J, González S. Confocal examination of non-melanoma cancers in skin excisions to potentially guide Mohs micrographic surgery without frozen histopathology. Journal of Investigative Dermatology 117: 1137-1143, 2001.
2. R. Hague, R. Contreras, M. P. McNicoll, E. C. Eckberg and D. B. Petitti, "Surgical margins and survival after head and neck cancer surgery," BMC Ear Nose Throat Disord 6: 2 (2006)
3. L. Jacobs, "Positive margins: The challenge continues for breast surgeons," Annals of Surgical Oncology 15(5): 1271-1272 (2008)
4. Patel Y G, Nehal K S, Aranda I, Li Y, Halpern A C, Rajadhyaksha M. Confocal reflectance mosaicing of basal cell carcinomas in Mohs surgical skin excisions. J. Biomedical Optics 12: 034027, 2007.
5. Al-Arashi M Y, Salomatina E, Yaroslaysky A N. Multimodal confocal microscopy for diagnosing nonmelanoma skin cancers. Lasers Surg Med 39:696-705, 2007.
6. Tilli M T, Cabrera M C, Parrish A R, Tone K M, Sidawy M K, Gallagher A L, Makariou E, Polin S A, Liu M C, Furth P A. Real-time imaging and characterization of human breast tissue by reflectance confocal microscopy. J. Biomed. Optics 12(5): 051901, 2007.
7. Kang D, Suter M J, Boudoux C, Yoo H, Yachimski P S, Puricelli W P, Nishioka N S, Mino-Kenudson M, Lauwers G Y, Bouma B E, Tearney G J. Comprehensive imaging of gastroesophageal biopsy samples by spectrally encoded confocal microscopy. Gastroint Endosc. 2010 January; 71(1):35-43.
8. Jain M, Shukla N, Manzoor M, Nadolny S, Mukherjee S. Modified full-field optical coherence tomography: A novel tool for rapid histology of tissues. J Pathol Inform. 2: 28, 2011.
9. Gareau D S, Li Y, Huang B, Eastman Z M, Nehal K S, Rajadhyaksha M. Confocal mosaicing microscopy in Mohs skin excisions: feasibility of rapid surgical pathology. J. Biomedical Optics 13: 054001, 2008.
10. Gareau D S, Patel Y G, Li Y, Aranda I, Halpern A C, Nehal K S, Rajadhyaksha M. Confocal mosaicing microscopy in skin excisions: a demonstration of rapid surgical pathology. J. Microscopy 233: 149-159, 2009.
11. Gareau D. S., The feasibility of digitally stained multimodal confocal mosaics to simulate histopathology, Journal of Biomedical Optics 14: 034050, 2009.
12. Bini J, Spain J, Nehal K, Hazelwood V, DiMarzio C, Rajadhyaksha M. Confocal mosaicing microscopy of human skin ex vivo: spectral analysis for digital staining to simulate histology-like appearance. J. Biomedical Optics 16: 076008, 2011.
13. Gareau D S, Karen J K, Dusza S W, Tudisco M, Nehal K S, Rajadhyaksha M. Sensitivity and specificity for detecting basal cell carcinomas in Mohs excisions with fluorescence confocal mosaicing microscopy. J. Biomedical Optics. 14: 034012, 2009.
14. Karen J K, Gareau D S, Dusza S W, Tudisco M, Rajadhyaksha M, Nehal K S. Detection of basal cell carcinomas in Mohs excisions with fluorescence confocal mosaicing microscopy. British J. Dermatol. 160: 1242-1250, 2009.
15. Abeytunge S, Li Y, Larson B, Toledo-Crow R, Rajadhyaksha M. Rapid confocal imaging of large areas of excised tissue with strip mosaicing. J. Biomedical Optics 16: 050504, 2011.
16. V. Becker, T. Vercauteren, C. H. von Weyhern, C. Prinz, R. M. Schmid and A. Meining, "High-resolution miniprobe-based confocal microscopy in combination with video mosaicing (with video)," Gastrointestinal Endoscopy 66: 1001-1007 (2007)
17. K. E. Loewke, D. B. Camarillo, C. A. Jobst and J. K. Salisbury, "Real-Time Image Mosaicing for Medical Applications," Medicine Meets Virtual Reality 15 125 (304-309) (2007)
18. Scope A, Mahmood U, Gareau D S, Kenkre M, Lieb J, Nehal K S, Rajadhyaksha M. In vivo reflectance confocal microscopy of shave biopsy wounds: feasibility of intraoperative mapping of cancer margins. British J. Dermatology 163: 1218-1228, 2010.

What is claims is:
1. A non-transitory computer readable medium having stored thereon computer-executable instructions which, when executed by a computer, cause the computer to perform a method for generating a strip mosaic image of an area of tissue with microscopic resolution, the method comprising:
 (i) acquiring, using a laser directed through an objective lens of a microscope, n line images of the tissue along an X axis, each of the line images having an equal length, while mechanically moving the tissue along a Y axis at a constant velocity in a first Y direction with continuous and uninterrupted motion, thereby producing a rectangular strip image comprising n line images along its length and having reduced illumination falloff along the Y axis, wherein each rectangular strip image has a width defined by the length of the line images and a length defining one dimension of the strip mosaic image;
 (ii) moving the tissue laterally along the X axis, by a distance equal to or less than the width of the strip image just produced;
 (iii) following said lateral moving, acquiring, using the laser, n line images along the X axis while mechanically moving the tissue along the Y axis at a constant velocity in a direction opposite to the previous Y direction with continuous and uninterrupted motion, thereby producing an additional rectangular strip image;

(iv) repeating steps (ii) and (iii), thereby producing a plurality of neighboring rectangular strip images; and (v) stitching the rectangular strip images together to generate the strip mosaic image of the tissue, said stitching comprising stitching each additional strip image along its length to the previous strip image.

2. The computer-accessible medium of claim 1, wherein the computer arrangement is further configured to synchronize the acquiring of the line images along the X axis with the moving of the tissue along the Y axis.

3. The computer-accessible medium of claim 1, wherein acquiring each line image comprises focusing the laser to a point on the tissue and optically scanning the laser across the tissue along the X axis.

4. The computer-accessible medium of claim 1, wherein acquiring each line image comprises focusing the laser into a line on the tissue along the X axis.

5. The computer-accessible medium of claim 1, wherein said stitching comprises:

registering each additional strip image pairwise to the previous strip image;

correcting illumination falloff along the X axis by averaging each strip image along its length, normalizing, and dividing each line image in the strip image by the normalized average falloff; and blending the additional strip image and the previous strip image in a region of overlap by a weighted average of overlapping pixels determined by pixel distance to the edge of the respective strip image.

6. A method for generating a strip mosaic image of an area of tissue with microscopic resolution, comprising:

(i) acquiring, using a laser directed through an objective lens of a microscope, n line images of the tissue along an X axis, each of the line images having an equal length, while mechanically moving the tissue along a Y axis at a constant velocity in a first Y direction with continuous and uninterrupted motion, thereby producing a rectangular strip image comprising n line images along its length and having reduced illumination falloff along the Y axis, wherein each rectangular strip image has a width defined by the length of the line images and a length defining one dimension of the strip mosaic image;

(ii) moving the tissue laterally along the X axis, by a distance equal to or less than the width of the strip image just produced;

(iii) following said lateral moving, acquiring, using the laser, n line images along the X axis while mechanically moving the tissue along the Y axis at a constant velocity in a direction opposite to the previous Y direction with continuous and uninterrupted motion, thereby producing an additional rectangular strip image;

(iv) repeating steps (ii) and (iii), thereby producing a plurality of neighboring rectangular strip images; and (v) stitching the rectangular strip images together to generate the strip mosaic image of the tissue, said stitching comprising stitching each additional strip image along its length to the previous strip image.

7. The method of claim 6, further comprising synchronizing the acquiring of the line images along the X axis with the moving of the tissue along the Y axis.

8. The method of claim 6, wherein acquiring each line image comprises focusing the laser to a point on the tissue and optically scanning the laser across the tissue along the X axis.

9. The method of claim 6, wherein acquiring each line image comprises focusing the laser into a line on the tissue along the X axis.

10. The method of claim 6, wherein said stitching comprises:

registering each additional strip image pairwise to the previous strip image;

correcting illumination falloff along the X axis by averaging each strip image along its length, normalizing, and dividing each line image in the strip image by the normalized average falloff; and blending the additional strip image and the previous strip image in a region of overlap by a weighted average of overlapping pixels determined by pixel distance to the edge of the respective strip image.

11. A system for generating a strip mosaic image of an area of tissue with microscopic resolution, comprising:

a microscope having a laser and an objective lens;

a translation stage to which the tissue is mounted; and a computer with a data acquisition card in communication with the microscope and the translation stage, the computer having stored thereon computer-executable instructions which, when executed, cause the computer to perform a method comprising:

(i) acquiring, using a laser directed through an objective lens of the microscope, n line images of the tissue along an X axis, each of the line images having an equal length, while mechanically moving the tissue along a Y axis at a constant velocity in a first Y direction with continuous and uninterrupted motion, thereby producing a rectangular strip image comprising n line images along its length and having reduced illumination falloff along the Y axis, wherein each rectangular strip image has a width defined by the length of the line images and a length defining one dimension of the strip mosaic image;

(ii) moving the tissue laterally along the X axis, by a distance equal to or less than the width of the strip image just produced;

(iii) following said lateral moving, acquiring, using the laser, n line images along the X axis while mechanically moving the tissue along the Y axis at a constant velocity in a direction opposite to the previous Y direction with continuous and uninterrupted motion, thereby producing an additional rectangular strip image;

(iv) repeating steps (ii) and (iii), thereby producing a plurality of neighboring rectangular strip images; and (v) stitching the rectangular strip images together to generate the strip mosaic image of the tissue, said stitching comprising stitching each additional strip image along its length to the previous strip image.

12. The system of claim 11, wherein the microscope further comprises a polygonal mirror focusing the laser to a point on the tissue and optically scanning the laser across the tissue along the X axis.

13. The system of claim 11, wherein the microscope further comprises a cylindrical lens focusing the laser into a line on the tissue along the X axis.

14. The system of claim 11, wherein the translation stage includes a linear encoder configured to transmit outputs to the data acquisition card for synchronizing the acquiring of the line images along the X axis with the moving of the tissue along the Y axis in real time.

15. The system of claim 11, wherein movement of the translation stage is controlled without a position encoder.

\* \* \* \* \*

UNITED STATES PATENT AND TRADEMARK OFFICE
CERTIFICATE OF CORRECTION

Page 1 of 1

PATENT NO. : 9,952,205 B2
APPLICATION NO. : 13/856672
DATED : April 24, 2018
INVENTOR(S) : Sanjee Abeytunge et al.

It is certified that error appears in the above-identified patent and that said Letters Patent is hereby corrected as shown below:

In the Claims

Column 13, Lines 7 through 18 in Line 1 of each of Claims 2-5, the text reading "computer-accessible" should read --computer readable--.

Signed and Sealed this
Seventeenth Day of July, 2018

Andrei Iancu
*Director of the United States Patent and Trademark Office*